United States Patent
Parthasarathy et al.

(10) Patent No.: US 11,031,121 B2
(45) Date of Patent: Jun. 8, 2021

(54) SYSTEM AND METHOD FOR INDICATING THE QUALITY OF INFORMATION TO SUPPORT DECISION MAKING

(71) Applicant: KONINKLIJKE PHILIPS N.V., Eindhoven (NL)

(72) Inventors: Vijay Parthasarathy, Tarrytown, NY (US); Alexander Adrianus Martinus Verbeek, Den Bosch (NL); Yuechen Qian, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 606 days.

(21) Appl. No.: 14/270,436

(22) Filed: May 6, 2014

(65) Prior Publication Data
US 2015/0324523 A1   Nov. 12, 2015

(51) Int. Cl.
G16H 40/20   (2018.01)
G16H 15/00   (2018.01)
G16H 10/60   (2018.01)
G16H 10/40   (2018.01)

(52) U.S. Cl.
CPC ............. *G16H 40/20* (2018.01); *G16H 10/40* (2018.01); *G16H 10/60* (2018.01); *G16H 15/00* (2018.01)

(58) Field of Classification Search
CPC ........ G06Q 50/22; G06Q 50/24; G16H 10/60; G16H 15/00; G06F 19/3481
See application file for complete search history.

(56) References Cited

U.S. PATENT DOCUMENTS

2010/0145720 A1\* 6/2010 Reiner ................ G06F 19/3443
                                                               705/2
2013/0018674 A1\* 1/2013 Bedi ...................... G06Q 10/00
                                                               705/3

OTHER PUBLICATIONS

Berner, E. "Clinical Decision Support Systems: State of the Art". 2009, Agency for Healthcare Research and Quality—Department of Health Services Administration: Rockville, Maryland.
Wears, R.L. et al, "Computer Technology and Clinical Work: Still Waiting for Godot". JAMA, 2005. 293(10): p. 1261-1263.
Arnott, D et al, "A Critical Analysis of Decision Support System Research". Journal Of Information Technology, 2005. 20(2): p. 67-87.
Orlikowski, W. "Knowing in Practice: Enacting a Collective Capability in Distributed Organizing". Organization Science, 2002. 13(3): p. 249-273.
Ellingsen, G. "The Role of Trust in Knowledge Management: A Case Study of Physicians at Work at the University Hospital of Northern Norway". Informing Science, 2003. 6.
Cicourel, A. et al. "The integration of distributed knowledge in collaborative medical diagnosis". Intellectual teamwork. Social and technological foundations of cooperative work, do, Editors. 1990, Erlbaum Ass: Hillsdale, NJ. p. 221-242.
Goergen, S. "Radiology Written Report Guideline Project". The Royal Australian and New Zealand College of Radiologists, 2011.

\* cited by examiner

*Primary Examiner* — Linh Giang Le

(57) ABSTRACT

A system for indicating the quality of a medical report including a medical report system which generates a medical score based on a clinician's interpretation of medical data, a portion of the medical report including text in a natural language; and a medical report grading device which processes the portion of text in natural language and generates one or more scores of one or more categories relating to the quality of the medical report.

22 Claims, 3 Drawing Sheets

SYSTEM AND METHOD FOR INDICATING THE QUALITY OF INFORMATION TO SUPPORT DECISION MAKING

The present application relates to clinical decision making. It finds particular application in conjunction with clinical decision support systems and will be described with particular reference thereto. However, it is to be understood that it also finds application in other usage scenarios and is not necessarily limited to the aforementioned application.

Clinical decision support systems (CDSS) have long been heralded as pivotal to improving the quality of health care. However, despite decades of research and excellent results for the stand-alone performance (in terms of sensitivity and specificity) of such systems, successful introduction and application of such systems in real clinical practice are extremely limited. An explanation for the lack of success is the invalid assumptions about the decision making process these systems are supposed to support. Typically, most of the design and evaluation of clinical decision support systems is based on the principles of rational decision making. However, qualitative field research shows that the underlying assumptions of rational decision making may bypass many aspects that impact the quality and efficiency of decision making in daily practice. One such an assumption of rational decision making is that the information and knowledge that goes in to the decision making process (or system) is objective and can be directly applied without any preprocessing.

For example, successful communication through written radiology reports depends on how well the radiologist conveys the results of image interpretation and analysis. There are many reasons why a radiologist's interpretation may be sub-optimal and need to be reviewed. First, it is known that the quality of readings of the radiologist are not uniform throughout the day—with a bias towards better quality in the mornings than in the evenings. Second, with many hospitals using tele-radiology services, the quality of radiology readings have more variations in style that it affects interpretation. Third, the reports generated by training radiologists may not be optimal during their training periods and may be in need for revision. In order to overcome this problem, typically, many radiology practices have a policy of re-reviewing a portion of their past scans. The problem with this approach is that this strategy does not ensure that all the scans that need a re-review are selected, thereby not ensuring complete quality control.

Currently, there are several indicators that may be used to indicate the quality and trustworthiness of reports or information used in the clinical decision support systems. For example, an indicator in medical practice often referred to by physicians is the seniority of a physician that produced the information, which may be rated by the number of years of practice. Other common examples to establish the quality and trustworthiness of reports and information are rating systems in internet applications (based on "wisdom of crowds" principle) that allow users of particular information to rate how useful or reliable the information was to them. Another, widely accepted example from the medical practice to determine the credibility of information from a physician is "case-volume", i.e. the number times a physician has produced similar information in the past.

There are several shortcomings to the current solutions. The most important shortcoming of the current practice is that establishing reliability involves a lot of human work and orchestration which causes inefficiency in the decision making process. Secondly, the indicators used, if any, are frequently extremely subjective (rating systems) or only serve as weak proxy indicators (years of practice) without incorporating measurement on the actual produced information. Finally, establishing a more reliable proxy indicator such as case-volume requires accurate registration. This is time consuming which leads to inefficiencies in healthcare. As such, volume measurements are only performed for a few selected types of reports or procedures.

The present application provides new and improved methods and systems which overcome the above-referenced problems and others.

In accordance with one aspect, a system for indicating the quality of a medical report is provided. The system includes a medical report system which generates a medical score based on a clinician's interpretation of medical data, a portion of the medical report including text in a natural language and a medical report grading device which processes the portion of text in natural language and generates one or more scores of one or more categories relating to the quality of the medical report.

In accordance with another aspect, a method for indicating the quality of a medical report is provided. The method includes receiving a medical report for a patient, a portion of the medical report being in a natural language, processing the portion of the medical report in natural language using a natural language processing engine, generating a score the medical report based on a plurality of categories relating to the quality of the medical report, and displaying the score of the medical report.

One advantage resides in the utilization of indicators to indicate the quality of reports and information.

Another advantage resides in the indication of the quality of the content, format, and trustworthiness of reports and information.

Another advantage resides in the reduction of human work involved in establishing the content, format, and trustworthiness of reports and information.

Another advantage resides in establishing quality indicators without the need for time consuming tailored registration procedures.

The invention may take form in various components and arrangements of components, and in various steps and arrangements of steps. The drawings are only for purposes of illustrating the preferred embodiments and are not to be construed as limiting the invention.

Figure 1:
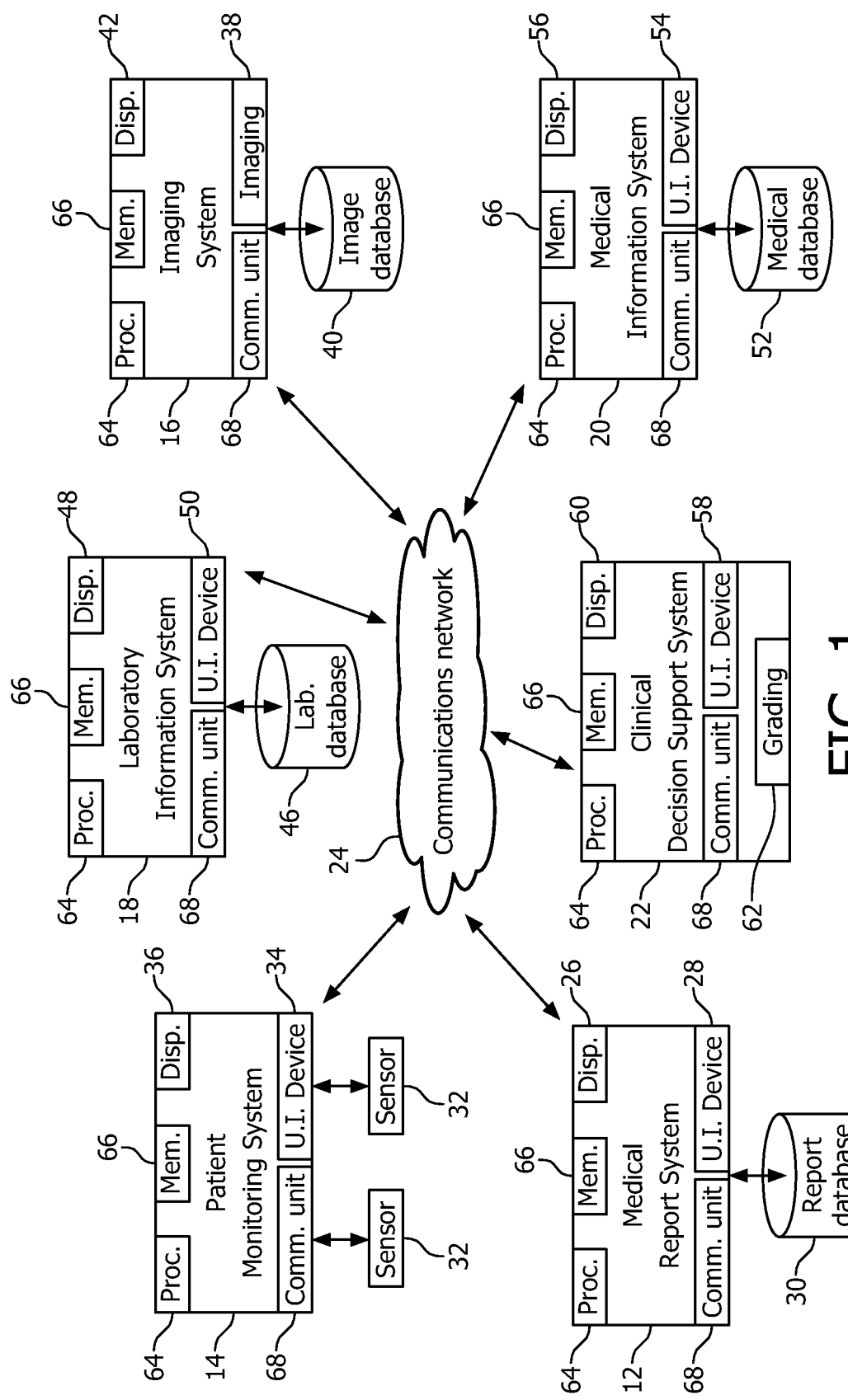
FIG. 1 is a block diagram of an IT infrastructure in accordance with the present application.

With reference to FIG. 1, a block diagram illustrates one embodiment of an information technology (IT) infrastructure 10 of a medical institution, such as a hospital. The IT infrastructure 10 suitably includes one or more medical reporting systems 12, one or more patient monitoring systems 14, one or more imaging systems 16, one or more laboratory information systems 18, a patient information system 20, a clinical decision support system 22, and the like, interconnected via a communications network 20. It is contemplated that the communications network 24 includes one or more of the Intranet, a local area network, a wide area network, a wireless network, a wired network, a cellular network, a data bus, and the like.

The medical report system 12 generates medical reports for patients (not shown) cared for by the medical institution. The medical report system 12 provides clinicians with the ability to interpret medical data and generate a medical report describing the physician's interpretation of the medical data. The medical report system 12 includes a display 26 such as a CRT display and a liquid crystal display, to a computer, to display the medical data to be interpreted and a user input device 28 such as a keyboard and a mouse, for the clinician to interpret the medical data and generate the medical report. The medical report system 12 acquires the medical data from the one or more patient monitoring systems 14, one or more imaging systems 16, one or more laboratory information systems 18, a patient information system 20, and the like. The report is an electronic file in a format, such as PDF, DOCX, DOC, and so on. In some embodiments, newly generated patient data and/or newly generated reports are saved in the IT infrastructure 10, such as in the patient information system 14. Further, in some embodiments, newly generated reports are electronically messaged to clinicians using, for example, email and/or printed using, for example, a laser printer, an inkjet printer and so on. The medical data suitable includes physiological data, laboratory data, image data, and the like. In response to the clinician requesting medical data, the medical report system 12 acquires and displays the requested medical data. The medical report system 12 generates an electronic file of a medical report in response to receiving the interpretation from a clinician. The medical report system 12 records the interpretation in a natural language into the electronic file, as well as links other medical data and information into the medical report. The medical report system 12 stores the medical report into a report database 30.

For example, the patient monitoring systems 14 obtain physiological data for patients (not shown) cared for by the medical institution. The physiological data suitably includes data indicative of one or more physiological parameters, such as heart rate, temperature, blood oxygen saturation, level of consciousness, concern, pain, urine output, and so on. Further, the patient data can be generated automatically and/or manually. As to the former, sensors 32, such electrocardiographic (ECG) electrodes, blood pressure sensors, SpO2 sensors, and so on, measuring physiological parameters of patients can be employed. As to the latter, user input devices 34 can be employed. In some embodiments, the patient monitoring systems 14 include display devices 36 providing users a user interface within which to manually enter the patient data and/or for displaying generated patient data to clinicians. The collected physiological data is concurrently transmitted to the patient information system 14 where the physiological data is displayed and stored. The medical report system 12 acquires and displays requested physiological data for a clinician to interpret. The medical report system 12 generates an medical report, for example, a physiological status report, in response to receiving the interpretation of the physician. Specifically, the medical report system 12 records the physiological status report in a natural language into an electronic file and stores the medical report into the report database 30.

Likewise, the imaging system 16 generates image data of a patient obtained using an image diagnosis apparatus 38 such as magnetic resonance imaging systems, nuclear medical imaging system, CT scanners, ultrasound systems, fluoroscopy, and the like. The image diagnosis apparatus 38 captures an image of a patient. The imaging system 16 generates image data reflecting the image of the patient and stores the generated image data to an image database 40. In some embodiments, the imaging system 16 include display devices 42 and a user interface 44 to adjust image reconstruction and acquisition parameters and/or for displaying generated image data to clinicians. The generated image data is also concurrently transmitted to the patient information system 14 where the image data is displayed and stored. The medical report system 12 acquires and displays requested image data for the clinician to interpret. The medical report system 12 generates a medical report, for example, a radiology report, in response to receiving the interpretation of the physician. Specifically, the medical report system 12 records the radiology report in a natural language into an electronic file and stores the medical report into the report database 30.

Similarly, the laboratory information system 18 generates laboratory data from tests which are done on clinical specimens in order to get information relating to the health of a patient as pertaining to the diagnosis, treatment, and prevention of disease. The laboratory testing including hematological blood testing, coagulation laboratory testing, chemical blood, urine and body fluid testing, microbiology testing, urine laboratory testing, serological laboratory testing, cytology, histology, and pathology testing, immunohematology and blood banking testing, and the like. The laboratory information system 18 generates laboratory data reflecting the laboratory tests and stores the generated laboratory data to a laboratory database 46. In some embodiments, the laboratory information systems 18 include display devices 48 and a user interface 50 within which to manually enter the laboratory data and/or for displaying generated laboratory data to clinicians. The collected physiological data is concurrently transmitted to the patient information system 14 where the physiological data is displayed and stored. The medical report system 12 acquires and displays requested laboratory data for the clinician to interpret. The medical report system 12 generates a medical report, for example, a pathology report, in response to receiving the interpretation of the clinician. Specifically, the medical report system 12 records the pathology report in a natural language into an electronic file and stores the medical report into a report database 30.

It should also be appreciated that the medical report system 12 is utilized to generate a variety of medical reports suitable including history and physical reports including a history of the present illness, past medical history, social history, and family medical history and an admission diagnosis and a plan for the patient's treatment, a consultation report including a brief history of the patient's illness, a specific physical exam depending on the particular type of consultation requested, and the consulting physician's impression and plan, an operative report including preoperative and postoperative diagnoses, the type of surgery or surgeries that were performed, the names of the surgeon(s) and attending nursing staff, the type of anesthesia and the name of the anesthesiologist, and a detailed description of the operative procedure itself, discharge summary report including a radiologist's findings and impression, a pathology report describing the findings of a tissue sample, laboratory report describes findings of examinations of bodily fluids such as blood levels and urinalysis, other miscellaneous reports including hospital reports, cardiac catheterizations, electrophysiology studies, phacoemulsification, autopsies and psychological assessments, and the like.

The patient information system 20 stores physiological data, image data, and laboratory data from the IT infrastructure 10, such as from the one or more patient monitoring systems 14, one or more imaging systems 16, one or more laboratory information systems 18, in one or more databases 52 of the IT infrastructure 10. The patient information system 20 also stores medical reports generated by the medical report system 12 in the one or more databases 52 of the IT infrastructure. It is also contemplated that the patient information system 20 stores physiological data, image, data, laboratory data, and medical reports generated from other IT infrastructures. In some embodiments, the patient information system 20 also stores physiological data, image data, laboratory data, and medical reports generated from user input devices 54 in the database 52 and/or allows stored physiological data, image data, laboratory data, and medical reports to be viewed on display devices 56. Examples of patient information systems include, but are not limited to, electronic medical record systems, departmental systems, and the like.

The CDSS 16 receives physiological data, image data, laboratory data, and/or medical reports from the IT infrastructure 10, such as from the one or more patient monitoring systems 14, one or more imaging systems 16, one or more laboratory information systems 18, report medical system 12 and/or the patient information system 14. It is also contemplated that the physiological data, image data, laboratory data, and/or medical reports can be received from user input devices 58, optionally with display devices 60 providing users a user interface within which to enter the physiological data, image data, laboratory data, and/or medical reports. Using the physiological data, image data, laboratory data, and/or medical reports, the CDSS 16 helps healthcare providers make clinical decisions. Specifically, the CDSS 16 displays patient treatment guidelines for a given patient in response to a query from clinicians and physiological data, image data, laboratory data, and/or medical reports. It is also contemplated that the CDSS perform or assist clinicians in clinical alerts and reminders, diagnostic assistance, prescription decision support, information retrieval, image recognition and interpretation, therapy critiquing and planning, and the like.

The CDSS 16 also includes a grading device 62 which provides a rating or a score of the quality of the medical reports. It is also contemplated that the grading device 62 is located on the medical report system 12 and/or the medical information server 14. Specifically, the grading device utilizes natural language processing (NLP) engines to process and analyze the medical report. After the medical reports are analyzed, the grading device 62 scores the medical report on various categories and sub-categories all relating to the quality of the medical report. The scoring of the medical reports are based on report content, report format, and report trustworthiness categories and sub-categories. Each of the individual categories contributes a certain part to the metrics of an overall score or rating based on the quality, clarity, and action-ability of the report, i.e. the three summary metrics are a weighted average of the individual scores of the categories and sub-categories. The grading device 62 ensures that sub-optimal medical reports are detected and flagged. If the aggregated scores or individual scores are below a selected threshold, the report is selected for re-review The grading device 62 also provides a visualization of the scores for each medical report. The visualization assesses and indicates the quality of the report content, report format, and report trustworthiness and also the three merit factors including clarity, quality, and action-ability.

It is also contemplated that the grading device 62 automatically flag radiologist's readings that are determined to be less than optimal. In another embodiment, the grading device 62 can be used to a quality assurance tool. For example, the grading device is utilized as a spell and grammar checker. For example, when a clinician finishes a medical report, the grading device 62 automatically checks the quality of the content of the report and alerts the clinician whether certain parts need further elaboration.

Referring back to FIG. 1, the components of the IT infrastructure 10 suitably include processors 64 executing computer executable instructions embodying the foregoing functionality, where the computer executable instructions are stored on memories 66 associated with the processors 64. It is, however, contemplated that at least some of the foregoing functionality can be implemented in hardware without the use of processors. For example, analog circuitry can be employed. Further, the components of the IT infrastructure 10 include communication units 68 providing the processors 64 an interface from which to communicate over the communications network 24. Even more, although the foregoing components of the IT infrastructure 10 were discretely described, it is to be appreciated that the components can be combined.

Figure 2:
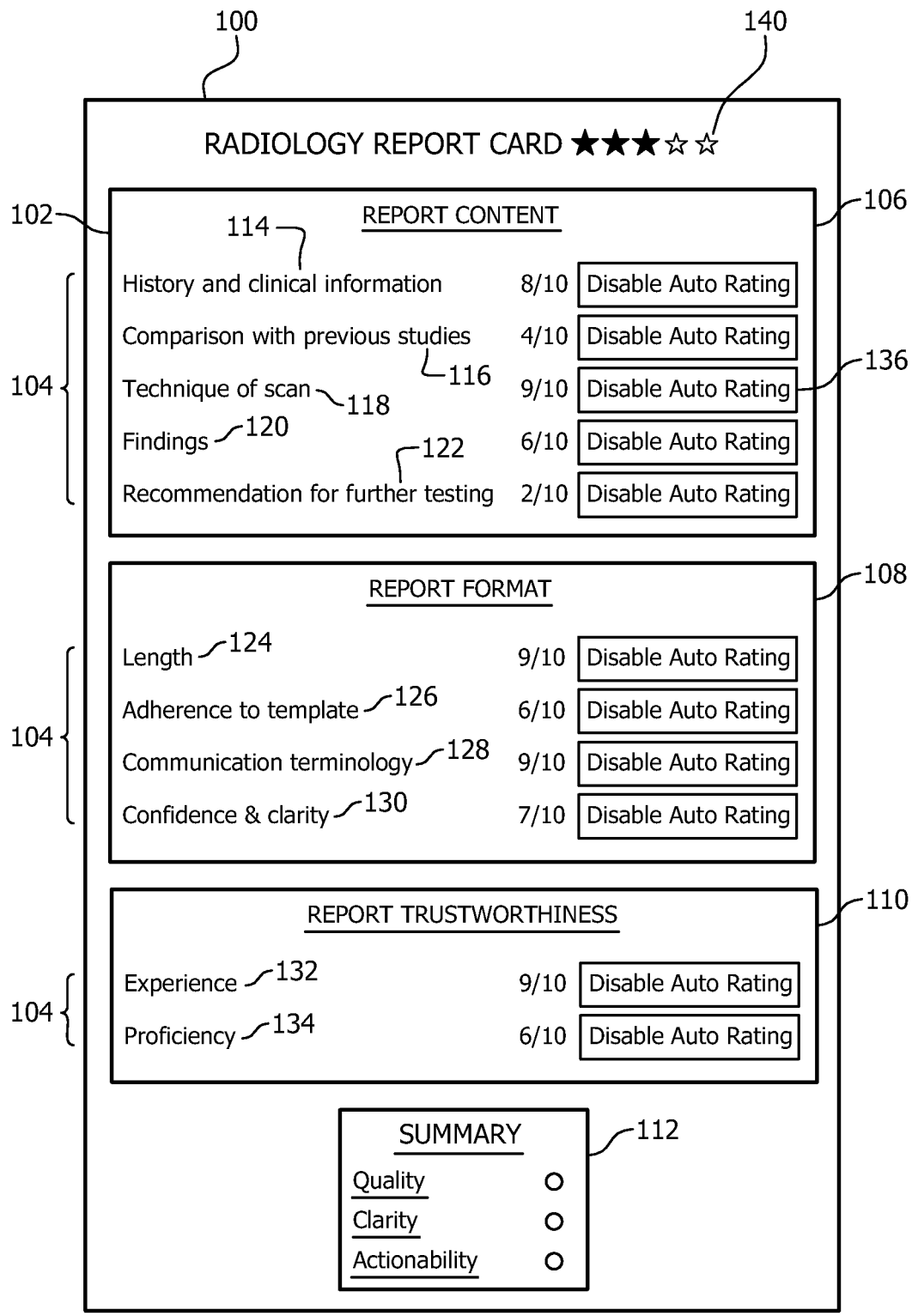
FIG. 2 is a visualization of a report card indicating the quality of medical report in accordance with the present application.

With reference to FIG. 2, a report card visualization indicating the quality of a medical report is illustrated. The report card 100 includes a plurality of categories 102 and each of the categories includes a plurality of scored sub-categories 104. As illustrated, the report card 100 grades a radiology medical report and include a report content category 106, a report format category 108, and a report trustworthiness category 110. The report card 100 also includes a summary category 112 which indicates the overall quality, clarity, and action-ability of the medical report. It is also contemplated that the report card 100 includes more or less categories 102 and sub-categories 104 which indicate the quality of medical reports. Additionally, although a radiology report card is illustrated it is also contemplated that the record card indicates the quality of various types of medical reports.

As mentioned above, the grade of the medical report is based on report content category 106, report format category 108, and report trustworthiness category 110. Each of the individual categories contributes a certain part to the metrics of quality, clarity and action-ability of the report, i.e. the three summary metrics are a weighted average of the individual scores. The report content category 102 includes a variety of sub-categories 104 that evaluate the quality of the content of the medical report.

The sub-categories 104 of the report content include history and clinical information 114, comparison with previous studies 116, techniques of the scan 118, findings 120, recommendation for further test 122, and the like. The history and clinical information sub-category 114 evaluates the content relevancy and the source of the content of the medical report. To evaluate the historical and clinical information of the medical report, the grading device 62 utilizes a NLP to extract clinical information of the medical report and reasons for the exam. This information is inputted into a matching algorithm that estimates how well the clinical information section of a report matches the reasons for the exam. The grading device 62 provides a numerical score indicating the quality of the content relevancy and the source of the content. The comparison with previous studies sub-category 116 evaluates the content of the medical report with the content of similar past medical reports. When comparing the content of the medical report with the content of previous studies, a NLP extracts the content of the medical report and a matching algorithm determines the similarity of the content between the current medical report and previous medical reports that are of a similar type. The grading device 62 provides a score indicated the similarity of the content of the current medical report with previous studies.

The technique of the scan sub-category 118 determines if the report describes the type of exam, contrast agent, procedure-related information and details of any immediate or delayed procedural complications and the management of the scan. To determine the technique of the scan, a NLP extracts DICOM headers (modality, protocol) from the image data and the description of protocols in the Techniques (Procedures) section and matches them accordingly. Depending on the existence of the information, the score for the technique of the scan sub-category is given according to the quality of the description of the technique of the scan. The findings sub-category 120 describes precise anatomical location, size, extent, shape of the findings. To describe the finding, existing medical ontologies containing comprehensive medical terms, including RadLex, SNOMED-CT, BIRADS are utilized. The ontologies are integrated into a NLP to extract medical terms from narrative reports. When radiological findings are detected by NLP in a piece of text, the grading device automatically checks whether there are occurrences of anatomical terms and measurements (size, shape and extent) in the surrounding text. If no anatomical terms and measurements occur the system assigns a score indicating the incompleteness of the findings. The recommendation for further testing sub-category 122 determines how the report will contribute to the diagnosis and management of the patient's current clinical problem. To determine how much the medical report contributes to the current clinical problem, a NLP evaluate the severity of the findings. Findings like cancer, carcinoma, invasive, and the like are reported to referrals. If those findings are present in a medical report, the system can check whether follow up action are also present. The grading device 62 scores the contribution of the medical report to the current clinical problem.

The sub-categories 104 of the report format include length 124, template 126, communication adherence 128, confidence and certainty 130, and the like. The length sub-category 124 determines how concise is the report while still conveying the information required to highlight key findings and to answer a clinical question. In order to accomplish this, a NLP considers the mean and median length of different radiology reports during a learning phase. During the learning phase, the system classifies the reports as optimal or as sub-optimal. The length of the current report under evaluation are compared against the mean and median lengths of other medical reports within the same category. A score is displayed based on how far from the mean is the current report to indicate the quality of length of the medical report. The template sub-category 126 determines if the report follows a specific template for standardized examination and disease process. Medical reports of certain categories follow specific medical report templates. To determine if the medical reports uses the correct template, a NLP compares the current medical report to the set of existing templates to see how well it fits into the suggested templates using a matching algorithm. The grading device 62 provides a score to indicate whether the medical report utilizes a correct template.

The communication adherence sub-category 128 evaluates the how accurate the medical report utilizes terminology with commonly agreed meaning and use of anatomically specific lesion location. To determine communication adherence, a NLP extracts the terms used in the medical report against medical ontologies to make sure that all the terms used adhere to the common terminology used for each disease process. If a certain term is detected that is not part of the dictionary, then that term will be flagged. A score is then provided to indicate the quality of the communication adherence of the medical report. The confidence and certainty sub-category 130 determines the confidence of the statements in the medical report. Typically, longer and more complex sentences tend to convey impression of less certainty than shorter and simply constructed sentence. To determine confidence and certainty, a NLP searches and finds the use-frequency of modifies like "might be consistence", "possibly represents", "clinical information correlated". A table of confidence/certainty words/phrases is collected from a corpus and computer linguistics tools like keyword matching and regular expression to detect occurrences of the defined words/phrases the medical report. A score is then provided based on the occurrence of detected confidence/certainty words/phrases to indicate the confidence a certainty of the medical report.

The sub-categories 104 of the report trustworthiness include an experience sub-category 132 and a proficiency sub-category 134. The experience sub-category automatically establishes how many times a producer of a report (information) has produced the same type of report (information) before. A score is then provided to indicate the experience of the producer of the medical report. The proficiency sub-category automatically establishes an indication for the quality of information of that producer based on a comparison to past outcomes achieved based on similar information generated by the same producer. The grading device 62 provides a score based on the comparison to indicate the proficiency of the producer of the medical report.

For example, when determining the trustworthiness of a radiology or pathology report, a NLP analyzes a current radiology report matches the text of the radiology report to known concepts in the ontology (for example reporting templates from the RSNA or College of American Pathologists). This identifies (1) which type of cases the report is dealing with (e.g. the staging of a lung cancer tumor) and (2) the actual value of the radiology determined stage for the lung cancer. Based on the matched concept, all reports from the same user are analyzed to identify how many times the clinician produced a similar reports (lung cancer staging report). This score is presented to the reader of the report in the report card 100 as a measure for the proficiency of the producer of the clinical report. Additionally, all of the medical records for all patients for which the radiologist produced a staging report in the past are analyzed in order to determine an indicator for quality for the radiologist's reported lung cancer stage in the past. This analysis uses a more elaborate ontology for the same concept, for example, clinical practice guidelines for lung cancer in which the radiology determined stage is related to the pathology determined stage which serves as gold standard benchmark. It is then determined how many times there is a mismatch between radiology stage and gold standard pathology stage. This score is presented to the reader of the radiology report as a measure for the proficiency of the producer of the stage information.

As another example, when determining the trustworthiness of a chemotherapy treatment proposal. A NLP processes a current treatment proposal created by a physician and matches the text to the concepts in the ontology (for example a clinical practice guidelines). This identifies which type of treatment proposal the plan is dealing with (e.g. a chemotherapy applied to reduce tumor size). Based on the matched concept, all reports from the same clinician are analyzed to identify how many times the clinician made a similar treatment decision. This score is presented to the reader/reviewer of the treatment plan in the report card. Additionally, the medical records for all patients for which the clinician earlier made similar decisions in the past are analyzed in order to determine an indicator for quality for the physician's treatment decision. This analysis uses a more elaborate ontology for the same concept, for example, clinical practice guidelines in which the treatment is related to anticipated tumor size reduction. It is then determined to which degree the tumor size reduction achieved over all patients from this particular clinician compares to the anticipated benchmark value for tumor size reduction embedded in the guideline. This score presented to the reader of the report card as a measure for the proficiency of the producer of the decision.

In the summary category 112, the scores from the different sub-categories 104 are weighted and averaged. The weighing of each of the different sub-categories may be predetermined based on specific clinical applications or adjusted by a reading clinician based on his or her preference. It should also be appreciated that the reading clinician may disable the automatic scoring 136 and manually input a sub-category score if the clinician deems necessary. From the weighted and averaged scores, the grading device 62 determines scores which represent of the clarity of the report, quality of the report, and action-ability of the report which are presented to the reader of the report card. The report card can also indicate a rating of the overall medical report. For example, the overall rating of the medical report may include visualization 140 which indicates the overall quality of the medical report. It should also be appreciated that if any of the scores or rating of the medical report is below a selected threshold, the medical report is selected for re-review and reason for re-review is shown.

Figure 3:
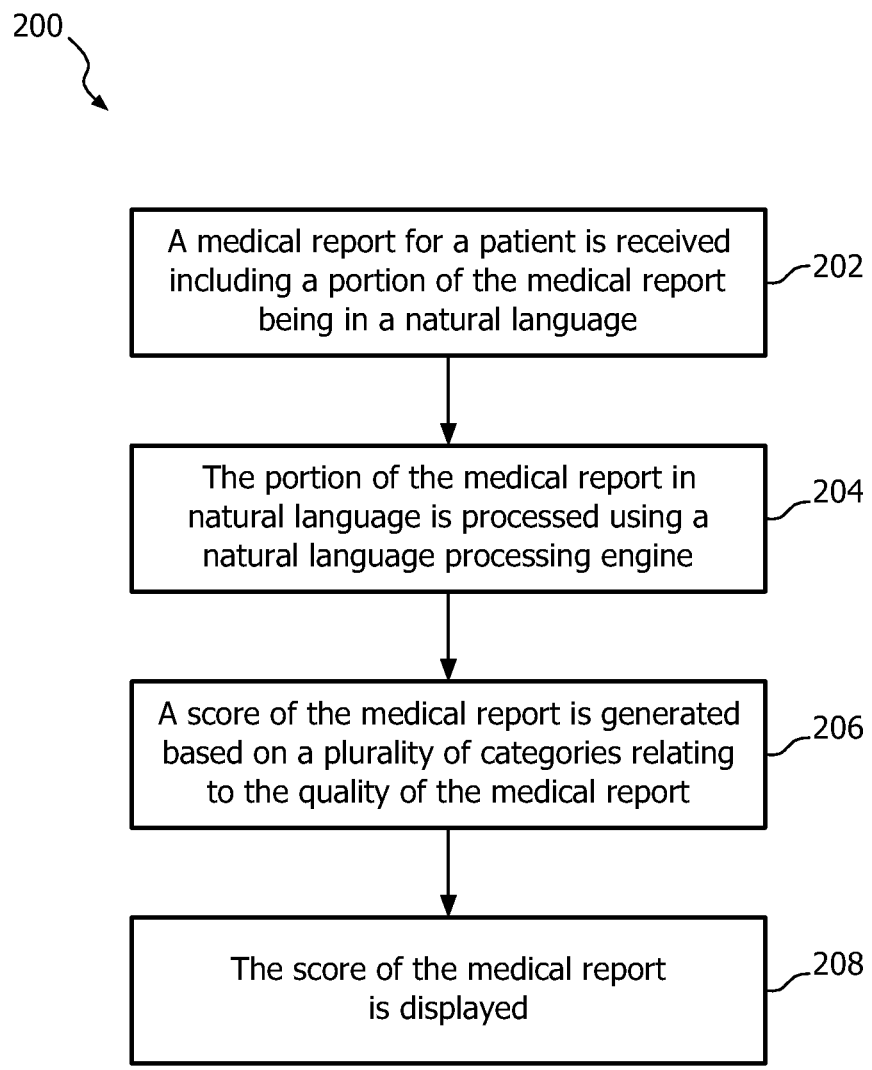
FIG. 3 is a flowchart diagram of a method for indicating the quality of medical reports in accordance with the present application.

1. With reference to FIG. 3, a method 200 for indicating the quality of medical reports is provided. In a step 202, a medical report for a patient is received including a portion of the medical report being in a natural language. In a step 204, the portion of the medical report in natural language is processed using a natural language processing engine. In a step 206, a score of the medical report is generated based on a plurality of categories relating to the quality of the medical report. In a step 208, the score of the medical report is displayed.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The Invention claimed is:

1. A medical report system comprising:
   a display;
   at least one user input device, the medical report system configured to receive a medical report from a clinician via the at least one user input device based on a clinician's interpretation of medical data, a portion of the medical report including text in a natural language; and
   a medical report grading device or processor programmed to, in response to the clinician finishing the medical report, automatically check quality of content of the medical report by:
      processing the portion of text in the natural language; and
      generating one or more scores of a plurality of categories relating to the quality of the medical report, wherein the plurality of categories include report content, report format, and report trustworthiness;
      and automatically alert the clinician of any part of the medical report that needs further elaboration.

2. The system according to claim 1, wherein each of the categories includes one or more sub-categories which are scored by the medical report grading device or processor.

3. The system according to claim 2, wherein each of the scores of the one or more categories and/or sub-categories are weighted and aggregated to generate one or more scores relating to at least one of the quality, a clarity, and an action-ability of the medical report.

4. The system according to claim 3, wherein the medical report grading device or processor is configured to calculate an overall rating of the medical report from at least one of the scores of the one or more categories and/or sub-categories and the one or more scores relating to at least one of the quality, clarity, and action-ability.

5. The system according to claim 3, wherein the one or more scores related to at least one of the quality, clarity, and action-ability of the medical report, and the overall rating of the medical report.

6. The system according to claim 1, wherein the trustworthiness of the medical reports is scored based on the experience and proficiency of the producer of the medical report.

7. The system according to claim 1, wherein the medical report grading device or processor is further programmed to control the display to display a visualization including the generated scores of the plurality of categories.

8. A system for indicating the quality of a medical report, the system comprising:
   a display;
   at least one user input device, the system configured to receive a medical report from a clinician via the at least one user input device based on a clinician's interpretation of medical data, a portion of the medical report including text in a natural language; and
   in response to the clinician's interpretation of medical data, one or more processors programmed to automatically check quality of content of the medical report by:
      processing a portion of a medical report in natural language using a natural language processing engine;
      generating a score of the medical report or of a treatment proposal in the medical report based on a plurality of categories relating to the quality of the medical report, the categories including of report content, report format, and report trustworthiness by determining a similarity of the processed portion of text with previous medical reports or previous treatment proposals of a similar type; and automatically alert the clinician of any part of the medical report that needs further elaboration.

9. The system according to claim 8, wherein the one or more processors are further programmed to:

weight and aggregate scores in the plurality of categories to generate an overall score indicative of the quality, a clarity, and an action-ability of the medical report.

10. The system according to claim 8, wherein each of the categories includes one or more sub-categories which are scored by the one or more processors.

11. The system according to claim 10, wherein each of the scores of the one or more categories and/or sub-categories are weighted and aggregated to generate one or more scores relating to at least one of the quality, a clarity, and an action-ability of the medical report.

12. The system according to claim 11, wherein the overall rating of the medical report is calculated from at least one of the scores of the one or more categories and/or sub-categories and the one or more scores relating to at least one of the quality, clarity, and action-ability.

13. The system according to claim 12, further including:

an input device configured to input the medical report;
a display configured to display the generated score; and
wherein the one or more processors are further programmed to:

generate a visualization including at least one of the scores of the one or more categories and/or sub-categories, the one or more scores relating to at least one of the quality, clarity, and action-ability of the medical report, and the overall rating of the medical report; and control the display to display at least one of the scores of the one or more categories and/or sub-categories, the one or more scores relating to at least one of the quality, clarity, and action-ability of the medical report, and the overall rating of the medical report.

14. A non-transitory computer readable medium carrying software which controls one or more processors to perform a method for indicating the quality of a medical report, the method comprising:

receiving a medical report for a patient via at least one user input device based on a clinician's interpretation of medical data, a portion of the medical report being in a natural language;

in response to the clinician finishing the medical report, automatically checking the quality of content of the medical report by:

processing a portion of the medical report in the natural language;

generating one or more scores of a plurality of categories relating to the quality of the medical report, wherein the plurality of categories include report content, report format, and report trustworthiness; and automatically alerting the clinician of any part of the medical report that needs further elaboration.

15. The non-transitory computer readable medium according to claim 14, wherein each of the categories includes one or more sub-categories which are scored.

16. The non-transitory computer readable medium according to claim 15, wherein each of the scores of the one or more categories and/or sub-categories are weighted and aggregated and further including:

generating one or more scores relating to at least one of the quality, a clarity, and an action-ability of the medical report.

17. The non-transitory computer readable medium according to claim 16, wherein the software carried by the non-transitory computer readable medium further controls the one or more processors to:

calculate an overall rating from at least one of the scores of the one or more categories and/or sub-categories and the one or more scores relating to at least one of the quality, clarity, and action-ability.

18. The non-transitory computer readable medium according to claim 16, wherein the software carried by the non-transitory computer readable medium further controls the one or more processors to:

control a display to generate and display a visualization including at least one of the scores of the one or more categories and/or sub-categories, the one or more scores relating to at least one of the quality, clarity, and action-ability of the medical report, and the overall rating of the medical report.

19. The non-transitory computer readable medium according to claim 14, wherein the software carried by the non-transitory computer readable medium further controls the one or more processors to:

flag sub-optimal portions of the medical reports for review.

20. The non-transitory computer readable medium according to claim 14, wherein the trustworthiness of the medical reports is scored based on the experience and proficiency of the producer of the medical report.

21. The non-transitory computer readable medium of claim 14, further comprising controlling a display to display the score of the medical report or scores for each of the quality of the medical report.

22. The non-transitory computer readable medium of claim 14, wherein the one or more scores are generated by determining a similarity of the processed portion of the medical report with previous medical reports of a similar type.

* * * * *